(12) United States Patent
Kaneko et al.

(10) Patent No.: US 7,416,899 B2
(45) Date of Patent: Aug. 26, 2008

(54) METHOD AND APPARATUS FOR MEASURING TRACE INGREDIENTS IN WATER

(75) Inventors: Emiko Kaneko, Miyagi (JP); Junichi Isoe, Miyagi (JP); Makoto Satoda, Tokyo (JP); Ryozo Goto, Tokyo (JP); Shinichi Akazawa, Tokyo (JP)

(73) Assignees: Tohoku Techno Arch Co., Ltd., Miyagi (JP); DKK-TOA Corporation, Tokyo (JP)

( * ) Notice: Subject to any disclaimer, the term of this patent is extended or adjusted under 35 U.S.C. 154(b) by 147 days.

(21) Appl. No.: 11/057,777

(22) Filed: Jan. 28, 2005

(65) Prior Publication Data

US 2005/0208669 A1     Sep. 22, 2005

Related U.S. Application Data

(63) Continuation of application No. PCT/JP03/09475, filed on Jul. 25, 2003.

(30) Foreign Application Priority Data

Jul. 29, 2002   (JP) ............................. 2002-220334

(51) Int. Cl.
*G01N 21/76* (2006.01)
*G01N 21/00* (2006.01)
*G01N 33/00* (2006.01)
*C12Q 1/68* (2006.01)

(52) U.S. Cl. ............... 436/172; 422/82.05; 436/138; 436/164; 435/6

(58) Field of Classification Search .......... 436/172, 436/138, 164; 422/82.05; 435/6
See application file for complete search history.

(56) References Cited

U.S. PATENT DOCUMENTS 4,810,655 A * 3/1989 Khalil et al. ............... 436/138

(Continued)

FOREIGN PATENT DOCUMENTS

JP          1-248058 A      10/1989

(Continued)

OTHER PUBLICATIONS

Isoe J, Kaneko E, Hoshi S, Okatsuka K. "Quenching Profile of Rhodamine B Accompanying Ionic Association with Heteropolymolybdate Ions", Bunseki Kagaku, 2002, vol. 51, No. 8, p. 657-659.*

(Continued)

*Primary Examiner*—Jill Warden
*Assistant Examiner*—Lore Ramillano
(74) *Attorney, Agent, or Firm*—Pantich Schwarze Belisario & Nadel LLP (57) ABSTRACT

A method and an apparatus are provided for measuring trace ingredients in water, which make it possible to perform detection and quantitative determination of silica, phosphorus or arsenic in a sample solution. The method includes adding a molybdate ion to a sample solution under an acidic condition, then adding a fluorescent counter cationic pigment thereto, and measuring the time required for the fluorescence emitted by the resultant solution to be attenuated to a prescribed intensity. The measuring apparatus includes an excitation light source which irradiates excitation light to the above-modified solution; a fluorescence detector which detects the fluorescence emitted by the solution; means for measuring the time required for the fluorescence detected by the fluorescence detector to be attenuated to a prescribed intensity; and control means for determining the concentration of silica, phosphorus or arsenic in the sample solution from the time measurement.

9 Claims, 5 Drawing Sheets

U.S. PATENT DOCUMENTS

| | | | | |
|---|---|---|---|---|
| 5,030,420 | A | * | 7/1991 | Bacon et al. ............. 422/82.07 |
| 5,034,189 | A | * | 7/1991 | Cox et al. ..................... 422/52 |
| 5,194,916 | A | * | 3/1993 | Hayashi ..................... 356/318 |
| 5,212,099 | A | * | 5/1993 | Marcus ....................... 436/172 |
| 2002/0031798 | A1 | * | 3/2002 | Anazawa et al. .............. 435/58 |

FOREIGN PATENT DOCUMENTS

| JP | 4-109166 A | 4/1992 |
|---|---|---|
| JP | 8-240584 A | 9/1996 |

OTHER PUBLICATIONS

Atkins WRG, Wilson EG. "CLV. the colorimetric estimation of minut amounts of compounds of silicon, of phosporous and of arsenic", Biochemical Journal, 1926, vol. 20, p. 1223-1228.*

Fusheng et al., The Determination of Trace Amounts of Phosphate in Natural Water by Flow Injection Fluorimetry, 1989, Analytical Letters, 22(15), 3081-3090.*

Johnson et al., Spectrophotometric Determination of Arsenite, Arsenate, and Phosphate in Natural Waters, 1972, Analytical Chimica Acta, 58, 289-299.*

Kan et al., Fluorophotometric Determination of Phosphate after Collection on a Membrane Filter as Ion Pair of Molybdophosphate with Rhodamine 6G, 1991, Analytical Sciences, 7, 87-91.*

Kirkbright et al., Spectrofluorimetric Determination of Orthophosphate as Rhodamine B Molybdophosphate, 1971, Analytical Chemistry, 43 (11), 1434-1438.*

A. Sabarudin et al., "Japan Society for Analytical Chemistry", *The $50^{th}$ Conference Lecture Abstract*, pp. 85, (2001).

Motomizu et al., *Analytical Chemistry*, vol. 33, pp. 116-118, (1984).

Motomizu et al., *The $63^{rd}$ Analytical Chemistry Symposium Lecture Abstract*, p. 7 (2002).

* cited by examiner

METHOD AND APPARATUS FOR MEASURING TRACE INGREDIENTS IN WATER

CROSS-REFERENCE TO RELATED APPLICATIONS

This application is a continuation of International Application No. PCT/JP2003/009475, filed Jul. 25, 2003, which was published in the Japanese language on Feb. 5, 2004, under International Publication No. WO 2004/011928 A1, and the disclosure of which is incorporated herein by reference.

BACKGROUND OF THE INVENTION

The present invention relates to a measuring method and a measuring apparatus for trace ingredients in water, particularly for detecting and quantitatively determining trace silica, phosphorus or arsenic contained in a sample solution.

An analyzing method in which heteropolymolybdic acid is formed by using molybdic acid is conventionally commonly used for detecting silica, phosphorus or arsenic contained in a sample solution. That is, the molybdenum blue absorptiometry is adopted in the Japanese Industrial Standards ("JIS"), and comprises the steps of adding molybdic acid to the sample solution to form heteropoly acid (molybdenum yellow) which emits yellow color, and quantitatively determining the blue color (molybdenum blue) available upon reduction of heteropoly acid by the absorptiometry.

For the purpose of measuring silica, phosphorus or arsenic, there is available a method based on association of heteropolymolybdate ion and counter ion. A method which applies collecting ion association product into a membrane filter has been reported. This method comprises the steps of collecting the ion association product of molybdosilicate ion formed by use of Malachite Green, dissolving the thus-collected product into methyl cellosolve with the filter, and introducing the dissolved product into FIA (flow injection analysis) of trace silica in water (A. Sabarudin, et al.: *Japan Society for Analytical Chemistry*, The 50th Conference Lecture Abstract, p. 85 (2001)). A method of detecting phosphorus in the same manner as above by the use of Rhodamine B as a counter cation has also been reported. There is also available an arsenic detecting method comprising the steps of collecting ion association product of tetraphenylphosphonium-molybdoarsenate into a filter, and dissolving the thus-collected product into tetramethylammonium hydroxide to measure the same by ETAAS (electrothermal atomic absorption spectrometry).

In addition, the following analyzing methods based on association of heteropolymolybdate ion and counter ion have been reported: one is a method for measuring phosphorus by detecting the amount of decrease in the fluorescence intensity in the FIA process by utilizing the fact that ion association with molybdophosphate ion causes a decrease in the fluorescence intensity of Rhodamine 6G (Motomizu, et al.: *Analytical Chemistry*, 33:116 (1984); and another is a method for measuring phosphorus from the amount of decrease in the fluorescence of Rhodamine B in the FIA process by using Rhodamine B as a counter ion simultaneously with polyvinyl alcohol (Motomizu, et al.: *The 63rd Analytical Chemistry Symposium Lecture Abstract*, p. 7 (2002)).

Along with the recent general tendency toward a higher degree of integrity of semiconductor, there is an increasing demand for reducing the impurities concentration in ultrapure water for the semiconductor industry to the minimum level. Particularly, development of a method for rapidly monitoring trace silica on a ppb level contained in ultrapure water at a high sensitivity and at a high accuracy is urgently needed. From the point of view of preserving the water quality against eutrophication of lake water and seawater, or of solving the problem of ground water containing arsenic becoming more serious at various localities in Asia, the demand for rapid, high-sensitivity and high-accuracy measurement of phosphorus and arsenic, having important meaning in environmental measurement, on a ppb level is more apparent.

However, the molybdenum blue absorptiometry conventionally popularly used for measuring silica, phosphorus or arsenic requires improvements including the use of a long optical path cell while reducing blanks to overcome the insufficient sensitivity, and has many problems in cost and equipment scale.

The method which applies collecting ion association product through a filter is not practicable since it requires complicated operation and much time, and furthermore, it employs an organic solvent of which the adverse effect on living organisms is feared.

As compared with the molybdenum blue absorptiometry and the like, the measurement of phosphorus by the above-mentioned FIA process contains some contrivances for increasing the sensitivity and simplifying the process. This method is however to measure the amount of decrease in the fluorescence intensity of Rhodamine B corresponding to the phosphorus concentration in the sample solution when a reaction solution have reached the fluorescence detector through the prescribed flow path system. It requires a complicated setting of various parameters including setting of a reaction coil length and setting of driving conditions for the liquid transporting pump, and a decrease in the measuring accuracy (resolution) for a sample solution having ingredients to be measured of lower concentrations or a very slight difference in concentration is inevitable.

BRIEF SUMMARY OF THE INVENTION

It is therefore an object of the present invention to provide a method and an apparatus for measuring trace ingredients in water, which make it possible to perform detection and quantitative determination of silica, phosphorus or arsenic in a sample solution simply, rapidly, at a high sensitivity, and at a high accuracy (high resolution).

It is another object of the present invention to provide a method and an apparatus for measuring trace ingredients in water capable of coping with automatic measurement of trace silica, phosphorus or arsenic in water.

The present inventors carried out extensive studies for solving the above-mentioned problems. As a result, they found a phenomenon in which along with ion association of heteropolymolybdate ion (resulting from the complexation reaction between molybdic acid and silicic acid, phosphoric acid or arsenic acid) with fluorescent counter cationic pigment, the fluorescence of the fluorescent counter cationic pigment gradually quenches typically on a time scale of several minutes. Particularly, they obtained a new finding that the quenching time depends upon concentration of silica, phosphorus or arsenic. The present inventors completed the present invention on the basis of this novel finding.

There are available many examples of research regarding the spectral shift of counter ion pigments caused by ion association. There is however no report on the dependency of the quenching time upon the concentration of silica, phosphorus or arsenic.

More specifically, the above-mentioned objects are achieved by the method and the apparatus for measuring trace ingredients in water of the present invention. In summary, a first aspect of the present invention relates to a method for measuring trace ingredients in water comprising the steps of adding a molybdate ion to a sample solution under an acidic condition, then adding a fluorescent counter cationic pigment thereto, and measuring the time required for the fluorescence emitted by the resultant solution to be attenuated to a prescribed intensity, thereby measuring the concentration of silica, phosphorus or arsenic in the sample solution. According to an embodiment of the present invention, the time measurement is started simultaneously with the addition of said fluorescent counter cationic pigment, and the time required for the fluorescence to be attenuated to a prescribed intensity is measured. According to another embodiment of the present invention, the time required for the fluorescence to be attenuated from a first intensity to a second intensity, after adding said fluorescent counter cationic pigment, is measured. The above-mentioned acidic condition may be achieved by mixing the sample solution with a strong acid.

According to a second aspect of the present invention, there is provided an apparatus for measuring trace ingredients in water comprising an excitation light source which irradiates excitation light to the solution obtained by adding a molybdate ion to a sample solution under an acidic condition and then adding a fluorescent counter cationic pigment to the resultant solution; a fluorescence detector which detects the fluorescence emitted by the solution; time measuring means for measuring the time required for the fluorescence detected by the fluorescence detector to be attenuated to a prescribed intensity; and control means for determining the concentration of silica, phosphorus or arsenic in the sample solution from the result of the time measurement by said time measuring means. According to an embodiment of the present invention, the time required from the addition of said fluorescent counter cationic pigment to the sample solution until the output of the fluorescence detector reaches a prescribed value is measured by means of said time measuring means. According to another embodiment of the present invention, the time required until the output of the fluorescence detector reaches from a first prescribed value to a second prescribed value, after adding said fluorescent counter cationic pigment to the sample solution, is measured by means of said time measuring means. According to still another embodiment of the present invention, the apparatus further comprises means for supplying the sample solution into a reaction container. In a further embodiment, the apparatus further comprises means for supplying an acidic solution containing said molybdate ion into the reaction container, and means for supplying a solution containing said fluorescent counter cationic pigment into the reaction container. In another embodiment, the apparatus further comprises means for supplying a strong acid into the reaction container, means for supplying a solution containing said molybdate ion into the reaction container, and means for supplying a solution containing said fluorescence cation pigment into the reaction container.

In these aspects of the present invention, when measuring the concentration of arsenic in the sample solution, an oxidizer can be added to the sample solution prior to adding said molybdate ion. As this oxidizer, iodate is suitably applicable. In this case, the apparatus of the present invention may further comprise means for supplying said oxidizer into the reaction container.

When measuring the concentration of silica in the sample solution in each of the above-mentioned aspects of the present invention, a decomposition agent of molybdophosphoric acid can be added after the addition of said molybdate ion, and thereafter said fluorescent counter cationic pigment can be added. As this molybdophosphoric acid decomposition agent, oxalic acid or tartaric acid is suitably applicable. In this case, the apparatus may further comprise means for supplying said decomposition agent of molybdophosphoric acid into the reaction container.

According to a preferred embodiment of the present invention, said fluorescent counter cationic pigment is Rhodamine B.

"Silica in the sample solution" as used in this specification includes each form of $SiO_2$, and $Si(OH)_n$. "Phosphorus in the sample solution" includes each form of $H_2PO_4^-$, $HPO_4^{2-}$ and $PO_4^{3-}$. "Arsenic in the sample solution" includes each form of $AsO_2^-$ and $AsO_4^{3-}$.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

The method and the apparatus for measuring trace ingredients in water of the present invention will now be described further in detail with reference to the drawings.

The method for measuring trace ingredients in water of the present invention comprises the steps of adding a molybdate ion to a sample solution under an acidic condition, then adding a fluorescent counter cationic pigment, measuring the time required until the fluorescence emitted from a resultant reaction solution is attenuated to a predetermined prescribed intensity, thereby detecting and quantitatively determining silica, phosphorus or arsenic in the sample solution.

More specifically, an embodiment of the method for measuring trace ingredients in water comprises the following steps:

1) Achieving an acidic condition of a sample solution;
2) Adding a molybdate ion to the sample solution;
3) Adding a fluorescent counter cationic pigment to the reaction solution resulting from step 2);
4) Irradiating excitation light to the reaction solution resulting from step 3), and monitoring the fluorescence intensity of the sample solution;

5) Starting a time measurement simultaneously with the addition of the fluorescent counter cationic pigment to the reaction solution in step 3);
6) Discontinuing the time measurement at the time when the fluorescence emitted by the reaction solution reaches a predetermined prescribed fluorescence intensity; and
7) Calculating the concentration of silica, phosphorus or arsenic in the sample solution on the basis of the interval between steps 5) and 6), i.e., the time from the start of the measurement to the discontinuance.

When the acidic condition of the sample solution is achieved in the above-mentioned step 1), a complex forming reaction between silicic acid, phosphoric acid or arsenic acid and the molybdate ion in the above-mentioned step 2) forms a heteropolymolybdic acid (molybdosilicic acid, molybdophosphoric acid, molybdoarsenic acid).

When the fluorescent counter cationic pigment is added to the reaction solution in step 3), the fluorescence of the fluorescent counter cationic pigment begins to be attenuated along with the ion association with the heteropolymolybdate ion. Simultaneously with the start of the time measurement in steps 4) and 5), gradual attenuation of the fluorescence emitted by the reaction solution is monitored.

Figure 1:
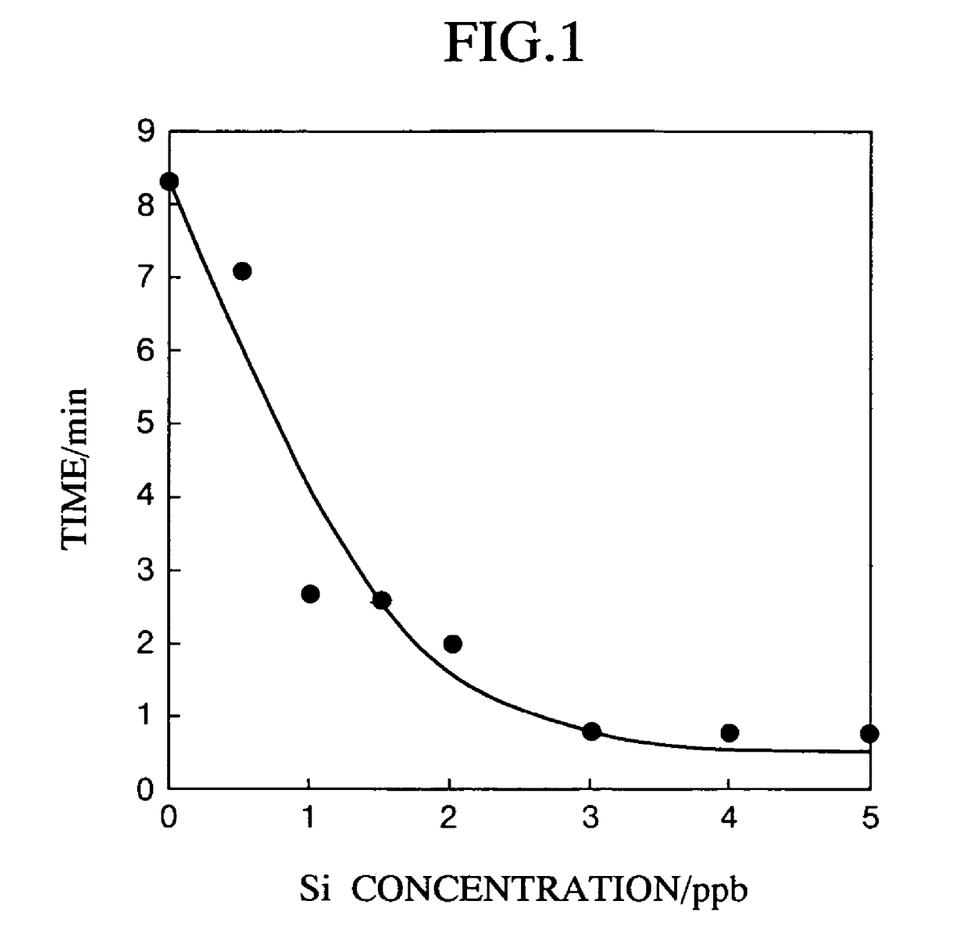
FIG. 1 is a graph illustrating the dependence of the fluorescence attenuation time of Rhodammine B caused by ion association on the silica concentration.
Figure 2:
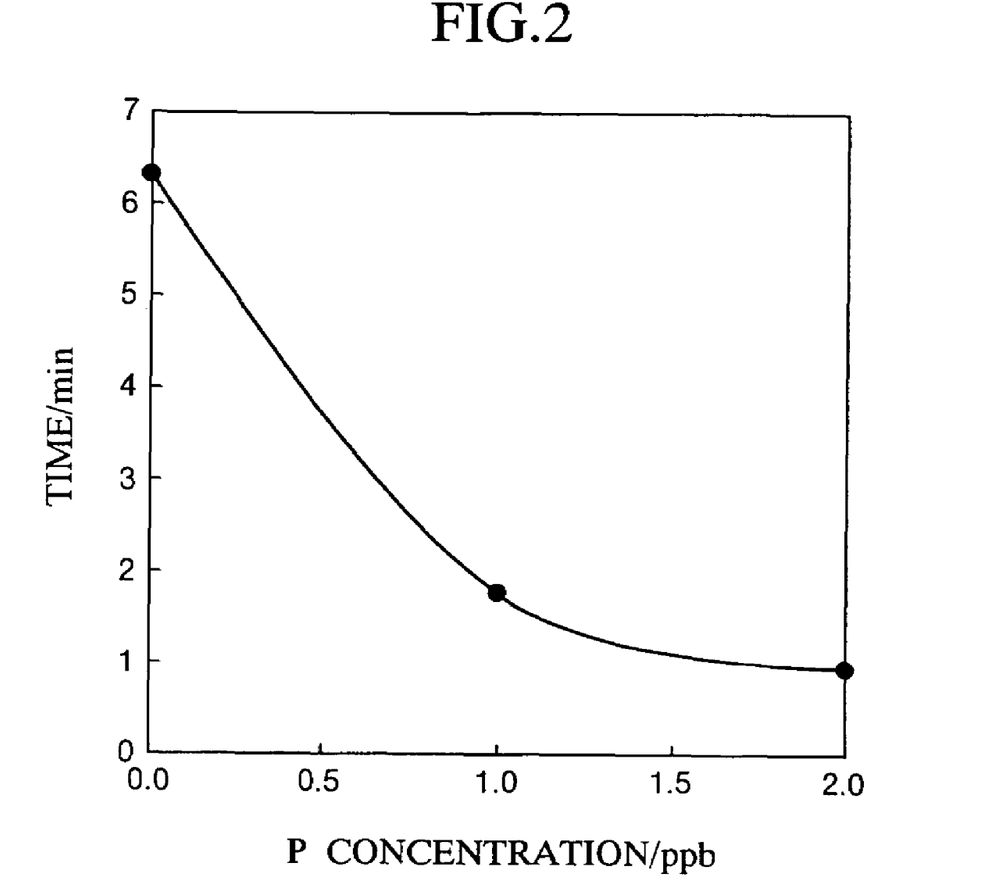
FIG. 2 is a graph illustrating the dependence of the fluorescence attenuation time of Rhodamine B caused by ion association on the phosphorus concentration.
Figure 3:
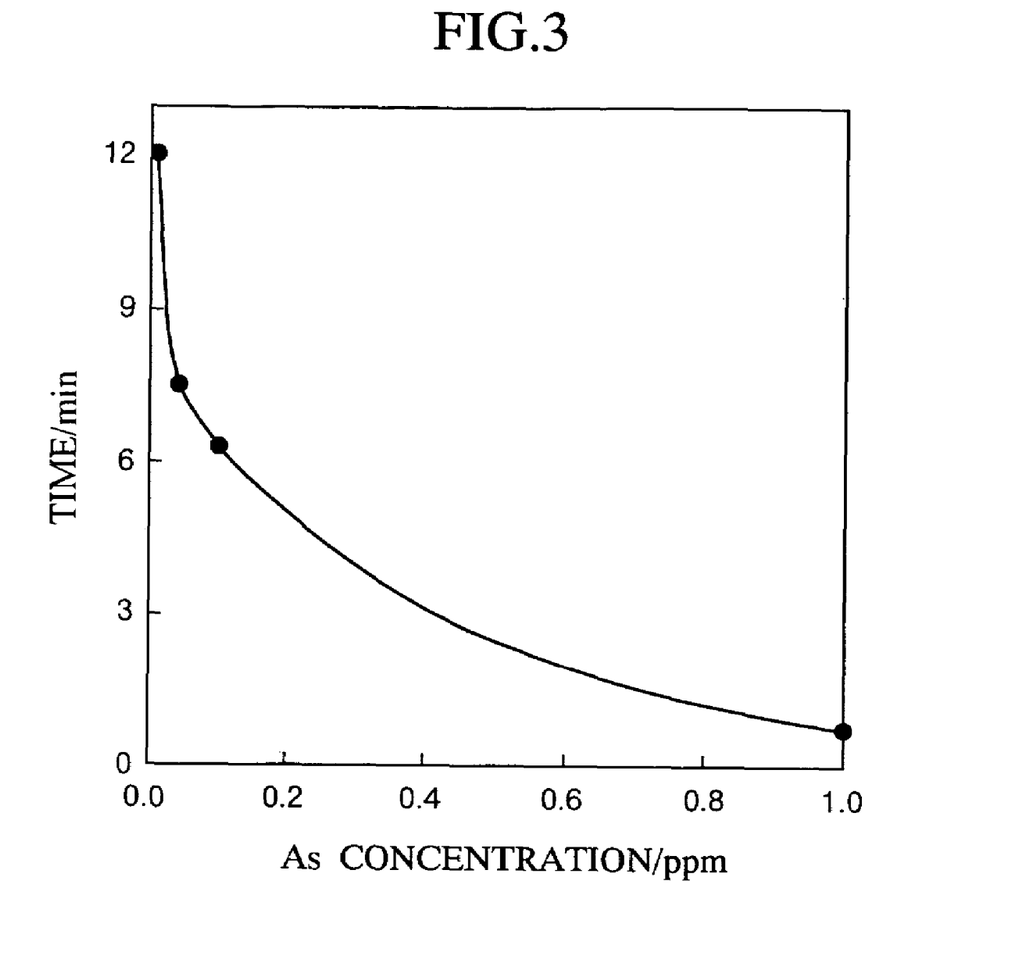
FIG. 3 is a graph illustrating the dependence of the fluorescence attenuation time of Rhodamine B caused by ion association on the arsenic concentration.

At the time when the fluorescence emitted by the reaction solution reaches a predetermined prescribed intensity in the above-mentioned step 6), through attenuation, the time measurement is discontinued, and the time from the addition of the solution containing the fluorescent counter cationic pigment to the attenuation of the fluorescence to the prescribed intensity is determined. This time depends upon the concentration of silica, phosphorus or arsenic contained in the sample solution (FIGS. 1, 2 and 3). In other words, a higher concentration of silica, phosphorus or arsenic leads to a shorter time required for the prescribed fluorescence intensity to be reached, and a lower concentration leads in contrast to a longer time until the prescribed fluorescence intensity to be reached.

In the above-mentioned step 7), the result of the time measurement is converted into the concentration of silica, phosphorus or arsenic in the sample solution. For this purpose, a calibration curve showing the correlation between the time of interval between steps 5) and 6) and the concentration of silica, phosphorus or arsenic is determined in advance by use of a desired reference solution (standard line).

The sample solution is subjected to formation of heteropolymolybdic acid under an acidic condition. The acidic condition of the sample solution can generally be achieved by mixing a strong acid in an effective amount for making the sample solution sufficiently acidic to form the heteropoly acid for the individual ingredients to be measured. This mixing may be accomplished by adding the strong acid into the reaction container containing the sample solution, or by adding the sample solution into the reaction container containing the strong acid, or by feeding the sample solution with the strong acid into the reaction container. The solution containing the molybdate ion to be added to the sample solution may be mixed with, for example, the strong acid to convert the solution into an acidic one. Strong acids applicable for achieving an acidic condition include sulfuric acid, hydrochloric acid and nitric acid. Sulfuric acid is preferable because of the highest fluorescence intensity and the high reproducibility.

In general, for the measurement of silica, phosphorus or arsenic, the acidic condition should preferably have a pH from 0.9 to 3.0 (sulfuric acid concentration: 0.4 to 0.02 M) representing a strong acidity.

Although not intending to limit, particularly when measuring the concentration of silica in the sample solution, more preferably, the acidic condition should have a pH from 0.9 to 1.2 (sulfuric acid concentration: 0.4 to 0.07 M). On the other hand, when measuring phosphorus or arsenic, more preferably, the acidic condition should have a pH from 0.9 to 1.4 (sulfuric acid concentration: 0.4 to 0.05 M).

Obstruction which may be caused in coexistence of ingredients to be measured is avoidable by setting the acidic condition further in detail, taking into account the difference in reactivity of the individual ingredients with the molybdate ion between degrees of acidity.

Applicable molybdate ions include ions coming from molybdates such as ammonium molybdate, sodium molybdate, and potassium molybdate. Ammonium molybdate is preferable in that it has a high purity. The molybdate ion is added in an amount appropriate for forming the heteropolymolybdate ion in the complex forming reaction with the ingredients to be measured (silica, phosphorus or arsenic) in the sample solution. Although not limitative, the concentration of the molybdate ion added to the reaction system should preferably be $2.5\times10^{-3}$ to $1.0\times10^{-2}$ M, or more preferably $5.0\times10^{-3}$ to $7.0\times10^{-3}$ M because of the high reproducibility.

As the fluorescent counter cationic pigment, any of the pigments known in the art may be selected for use with no particular limitation, so far as the pigment spectrum generated by association with heteropoly acid ion is applicable, as well as the quenching time of the fluorescence depends upon the concentration of silica, phosphorus or arsenic contained in the sample solution, and it is applicable for the measurement of the concentration of silica, phosphorus or arsenic contained in the sample solution from properties thereof. Rhodamine B is preferable in that it has a high fluorescence intensity, is stable in the highly acidic condition, is available at a low cost, and has a high purity.

The fluorescent counter cationic pigment should be added in an amount sufficient to achieve ion association with heteropolymolybdate ion in the reaction solution. An amount in excess relative to the concentration of silica, phosphorus or arsenic in the sample solution is usually added. Although not limitative, the concentration of the fluorescent counter cationic pigment added to the reaction system should preferably be $4.4\times10^{-7}$ to $7.8\times10^{-6}$ M, or more preferably, $2.0\times10^{-6}$ to $5.8\times10^{-6}$ M.

According to another embodiment of the present invention, the method for measuring trace ingredients in water comprises the following steps 8) and 9) in place of the above-mentioned steps 5) and 6):

8) Starting a time measurement, after adding the fluorescent counter cationic pigment to the reaction solution in the above-mentioned step 3), at the time when the fluorescence of the reaction solution reaches, through attenuation, a predetermined first fluorescence intensity; and
9) Discontinuing the time measurement at the time when the fluorescence of the reaction solution reaches, through attenuation, a predetermined second fluorescence intensity.

According to this embodiment, a more accurate measurement of the quenching time is ensured by excluding a region which may become unstable immediately after the addition of the fluorescent counter cationic pigment to the reaction solution. In this case, the correlation between the time of interval between steps 8) and 9) and the concentration of silica, phosphorus or arsenic in the form of a calibration curve may be determined in advance, thereby determining the concentration of silica or phosphorus in the sample solution.

According to a more preferable embodiment regarding the measurement of the arsenic concentration in the sample solution, the method for measuring trace ingredients in water further comprises the following step 10):

10) Adding an oxidizer to the sample solution prior to adding the molybdate ion to the sample solution in the above-mentioned step 2).

This makes it more reliable to change substantially all arsenic in the sample solution into a pentavalent chemical form (As(V)). Since As(III) ion does not generate heteropoly acid ion with molybdic acid, the oxidizer in an amount sufficient to cause conversion of arsenic in the sample solution into a pentavalent chemical form should be added. The above-mentioned step 10) may be inserted before the above-mentioned step 1), i.e., before setting the acidic condition of the sample solution, or may be inserted after the above-mentioned step 1) and before step 2), i.e., prior to adding the molybdate ion after setting the acidic condition of the sample solution.

The oxidizer may be selected for use from among those known in the art which can change arsenic into a pentavalent chemical form, and match the above-mentioned object. Applicable oxidizers include oxygen such as hydrogen peroxide; hypochlorous acid or salt thereof such as sodium hypochlorite; chlorous acid or salt thereof such as sodium chlorite; halogen acid or salt thereof including, for example, chloric acid or salt thereof such as sodium chlorate and potassium chlorate, iodic acid and salt thereof such as sodium iodate and potassium iodate; perhalogen acid or salt thereof including, for example, chloric acid and salt thereof such as sodium perchlorate, potassium perchlorate and ammonium perchlorate, iodic acid and salt thereof such as sodium periodate, potassium periodate and ammonium periodate; persulfuric acid and salt thereof such as sodium persulfate and potassium persulfate; peroxysulfuric acid and salt thereof; pernitric acid and salt thereof; percarbonic acid and salt thereof, perboric acid and salt thereof such as sodium perborate; and organic peracid such as performic acid, peracetic acid, m-chloroperbenzoic acid. Preferable oxidizers include salt of halogen acid including, for example, chlorate such as sodium chlorate and potassium chlorate, iodate such as sodium iodate and potassium iodate, or more preferably, iodate such as sodium iodate and potassium iodate.

According to still another embodiment of the present invention, when it is necessary to eliminate the effect of obstruction by coexisting phosphorus, the method for measuring trace ingredients in water further comprises the following step 11):

11) When measuring the concentration of silica in the sample solution, and if phosphorus is considered to coexist in the sample solution, adding a decomposition agent of molybdophosphoric acid after adding the molybdate ion to the sample solution in the above-mentioned step 2).

This decomposes molybdophosphoric acid generated simultaneously with molybdosilicic acid. Subsequently, in the above-mentioned step 3), the fluorescent counter cationic pigment is added to cause an ion association of the molybdosilicate ion and the fluorescent counter cationic pigment. As the decomposition agent of molybdophosphoric acid, any agent capable of being used for this purpose may be applied without limitation. Particularly, oxalic acid solution or tartaric acid solution is suitable because of the high decomposition ability. However, when measuring the concentration of silica, for example, in ultrapure water for semiconductor industry, coexistence of phosphorus can usually be disregarded. The above-mentioned step 11) is therefore omitted in such a case.

The prescribed fluorescence intensity at which the time measurement is discontinued in the above-mentioned step 7) and the prescribed second fluorescence intensity in the above-mentioned step 9) can be set in view of measurable range (optimum measuring range) of the fluorescence detector. The measuring time can be controlled by appropriately changing, for example, the concentration of the fluorescent counter cationic pigment applied to the reaction system. It is not desirable from the point of view of measuring accuracy to set the above-mentioned prescribed fluorescence intensity outside the optimum range of the fluorescence detector. In general, a higher concentration of the fluorescent counter cationic pigment leads to a longer period of time until attenuation to the prescribed fluorescence intensity and a higher measuring accuracy (resolution) relative to the difference in concentration of silica, phosphorus or arsenic, but an excessively long time is not desirable for rapidity of measurements. Optimum reaction conditions should preferably be predetermined in accordance with a specific object and preferential matters (accuracy, time and the like) as a person skilled in the art carries out as routine operations. In the present invention, it is also possible to measure the time throughout the entire range from the beginning of the fluorescence emission of the reaction solution to the quenching may be measured. The prescribed first fluorescence intensity in the above-mentioned step 8) may be set relative to the second fluorescence intensity described above so as to exclude, from the result of time measurement, the region in which the reaction system becomes unstable after the addition of the fluorescent counter cationic pigment.

In a preferred embodiment of the present invention, when measuring silica or phosphorus, the sample solution is introduced into a reaction container suitable for detecting fluorescence of the content (fluorescence detecting cell), and an aqueous sulfuric acid solution is added to the sample solution which is then shaken to achieve an acidic condition. Then, an aqueous ammonium molybdate solution in an amount sufficient to form the heteromolybdate ion under the acidic condition is added and the mixture is shaken (left for a few minutes if desired). Then, an aqueous Rhodamine B solution in an amount sufficient to cause the ion association with the heteromolybdate ion is added to this reaction solution, and the detection of the fluorescence emitted from the resultant reaction solution is started. The time measurement is started simultaneously with the addition of the aqueous Rhodamine B solution, or at the time when fluorescence emitted by the reaction solution reaches, through attenuation, the prescribed intensity. Thereafter, the time measurement is discontinued at the time when the fluorescence emitted by the reaction solution reaches the prescribed light quantity. The concentration of silica or phosphorus in the sample solution can be calculated from the result obtained of the time measurement by the utilization of the predetermined relationship between the concentration of silica or phosphorus and the time.

When phosphorus is considered to coexist upon measuring silica in the sample solution, an ammonium molybdate solution is added to the sample solution which is then shaken (left for a few minutes as desired), and then, an oxalic acid or a tartaric acid solution in an amount sufficient to permit decomposition of molybdophosphoric acid is added. The resultant solution is shaken (left for a few minutes as desired). Subsequently, a Rhodamine B solution in an appropriate amount may be added to this reaction solution.

When measuring arsenic, on the other hand, in a preferred embodiment, the sample solution is introduced into a reaction container suitable for detecting fluorescence of the content (fluorescence detecting cell), and an aqueous potassium iodate solution in an amount sufficient to convert arsenic into a pentavalent chemical form is added to the sample solution which is then shaken. An aqueous sulfuric acid solution is added to the resultant solution, and the mixture is shaken to achieve an acidic condition. Then, an aqueous ammonium molybdate solution in an amount sufficient to form the heteropolymolybdate ion under an acidic condition is added and the mixture is shaken (left for a few minutes as desired). Then, an aqueous Rhodamine B solution in an amount sufficient to cause the ion association with the heteropolymolybdate ion is added to the reaction solution, and the detection of fluorescence emitted by the resultant reaction solution is started. The time measurement is started at the same time as the addition of the aqueous Rhodamine B solution or at the time when the fluorescence emitted by the reaction solution reaches, through attenuation, the prescribed intensity. Thereafter, the time measurement is discontinued at the time when the fluorescence emitted by the reaction solution reaches the prescribed light quantity. The concentration of arsenic in the sample solution can be calculated from the result of the time measurement thus obtained by the utilization of the predetermined relationship between the arsenic concentration and the time.

When ingredients to be measured are considered to coexist, it is conceivable to avoid obstruction caused by coexisting ingredients by setting acidic conditions further in detail by the utilization of the difference in reactivity of the individual ingredients to be measured in the reaction with molybdate ion depending upon the degree of acidity.

According to the method for measuring trace ingredients in water of the present invention, it is possible to detect and quantitatively determine trace silica, phosphorus or arsenic on a ppb level, easily, rapidly, at a high sensitivity and at a high accuracy (high resolution).

The fluorometry provides a sensitivity far higher than in the absorptiometry, and by being based on the fluorometry, the measuring sensitivity is remarkably improved as compared with a method such as the molybdenum blue absorptiometry. Also, it does not require complicated operations, such as membrane filter collection of ion association products.

When detecting, with a fluorescence detector, the amount of decrease in the fluorescence intensity of the fluorescent counter cationic pigment dependent upon the concentration of ingredients to be measured as in the measurement of phosphorus by the conventional FIA process, if the difference in the fluorescence intensity is to be detected, it is inevitable that a decrease in resolution relative to the sample solution in a region of a lower concentration and a slight difference in concentration is caused by the characteristics of the amplification circuit of output of the fluorescence detector.

When silica, phosphorus or arsenic in the sample solution is measured on the basis of the measured value of the time required until the fluorescence intensity is attenuated to a prescribed value, the measuring accuracy (resolution) particularly for a lower-concentration sample solution and a slight difference in concentration does not decrease but is extremely good.

Figure 4:
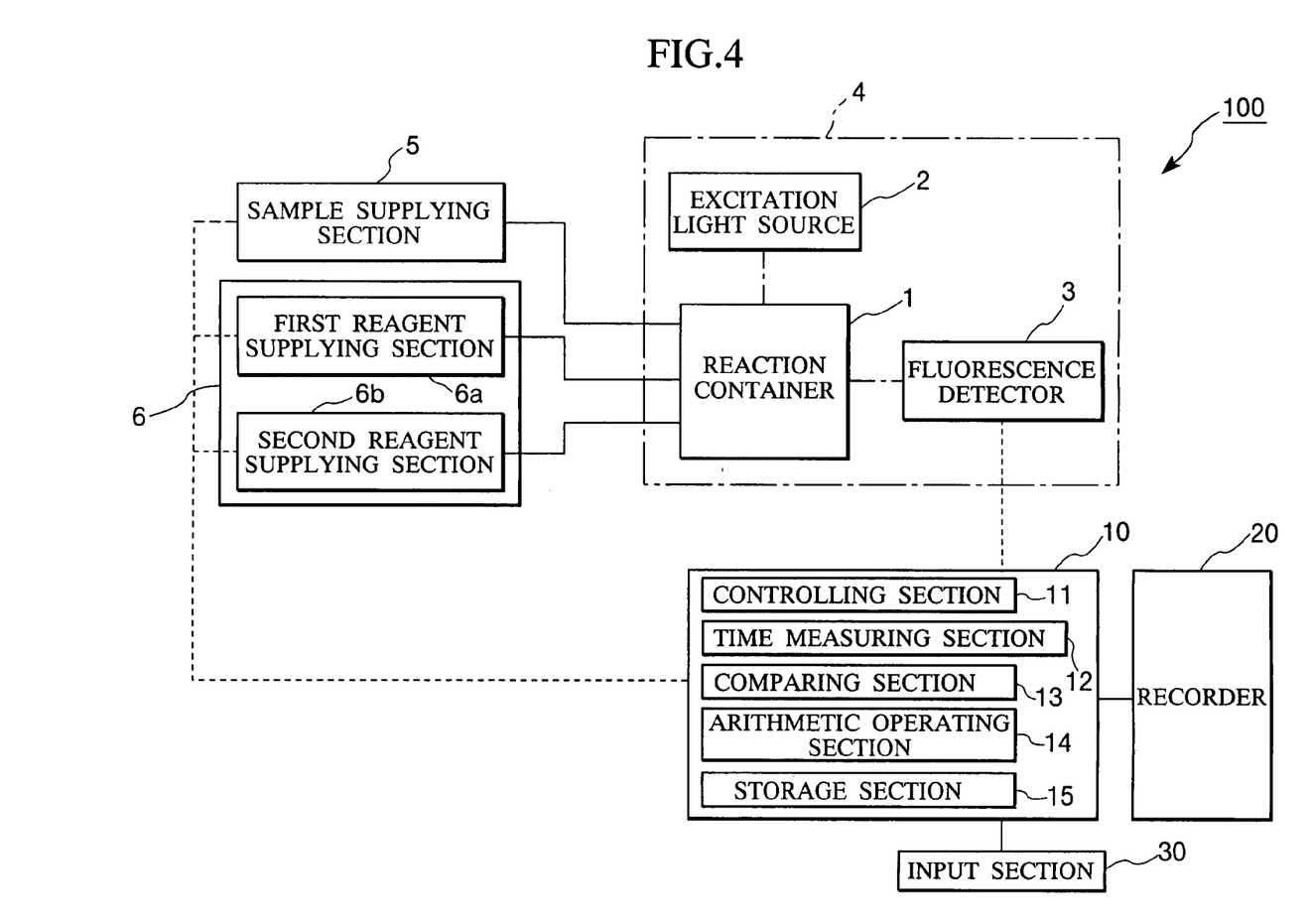
FIG. 4 is a schematic configuration diagram of an embodiment of the apparatus of the present invention for measuring trace ingredients in water.

An embodiment of the measuring apparatus which materializes the measuring method of trace ingredients in water of the present invention and can cope with automatic measurement will now be described. FIG. 4 illustrates a schematic configuration of the measuring apparatus 100.

The measuring apparatus 100 comprises, in accordance with the present invention, an excitation light source 2 which irradiates excitation light onto a reaction solution obtained by adding a molybdate ion to a sample solution under an acidic condition and then adding a fluorescence counter cationic pigment thereto; a fluorescence detector 3 which detects fluorescence emitted by the reaction solution; measuring means 12 for measuring the time required until fluorescence emitted by the reaction solution detected by the fluorescence detector 3 is attenuated to a prescribed intensity; and control means 10 for determining the concentration of silica, phosphorus or arsenic in the sample solution from the result of the time measurement carried out by the time measuring means 12.

More specifically, the measuring apparatus 100 automatically supplies the sample solution and various reagent solutions into a reaction container (reactor) 1 from sample supplying means (sample supplying section) 5 and reagent supplying means 6 in accordance with a prescribed procedure. The excitation light source 2 is arranged so as to irradiate excitation light onto the solution in the reaction container 1, and the fluorescence detector 3 is arranged so as to detect the fluorescence emitted by the solution in the reaction container 1. Although not limitative, control of all the component elements of the measuring apparatus 100 is comprehensively performed by a controller (control circuit) 10 serving as the control means in this embodiment.

At least the reaction container 1, the excitation light source 2, and the fluorescence detector 3 should preferably be housed in a light shielding case 4 serving as light shielding means. The reaction container 1 should preferably have a temperature control mechanism (not shown) so that the reaction solution maintains a constant temperature during the measuring period. A stirring mechanism which can sufficiently mix and stir the solution in the reaction container 1 at a proper timing may be provided. These temperature control mechanism and stirring mechanism may be selected from among those known and used commonly in the art.

At least a part of the reaction container 1 is permeable or open so as to allow the excitation light from the excitation light source 2 to reach the solution therein, and at least a part thereof is permeable or open so as to allow the fluorescence of a detectable wavelength (wavelength of fluorescence) emitted by the solution to reach the fluorescence detector 3. The reaction container may be one of those generally applied as a cell for detecting fluorescence in the art.

The excitation light source 2 is controlled so as to irradiate the excitation light having a predetermined wavelength onto the reaction solution at least simultaneously with the addition of Rhodamine B solution to the reaction solution or at a proper timing thereafter. Applicable excitation light sources 2 include a mercury lamp, a xenon flash lamp, an ultraviolet light source such as an ultraviolet lamp based on silent discharge, and a visible light source such as a tungsten lamp.

The fluorescence detector 3 is connected to the controller (control circuit) 10 via an amplifier. Current or voltage generated by the fluorescence detector on detecting the light is transmitted to the controller 10 as a voltage signal amplified by the amplifier. Applicable fluorescence detectors 3 include a photoelectric conversion element such as a photodiode, a phototransistor, an avalanche photodiode and a photoelectron multiplier.

The controller 10 has a controlling section 11 which controls the operation of the controller 10; time measuring means (time measuring section) 12; a comparing section (comparator) 13; an arithmetic operating section 14; and a storage section 15. The controlling section 11 controls driving of the individual component elements as specified in the measuring procedure, for example, in accordance with a program stored in the storage section 15. The controller 10 has an interface element (not shown) for transmitting and receiving signals to and from the external devices. The controlling section 11, the time measuring section 12 and the arithmetic operating section 14, for example, may of course be integrated into a microcomputer and the like. As the storage section 15, any storing means capable of storing data may be used with no particular limitation. It should however preferably be an electronic storage element (memory) from the point of view of compactness, lightness in weight and cost.

A recorder 20 is communicably connected to the controller 10. The recorder may be an arbitrary one which records the result of measurement onto a recording medium such as paper and outputs the same, or displays the same on a display such as an LCD. An input section 30 for starting or ending the measurement, or entering various setting values is communicably connected to the controller 10.

The sample supplying section 5 has a sample solution storing section (not shown), and sample solution quantifying/adding means, and quantifies and supplies the sample solution in a prescribed amount to the reaction container 1 in accordance with the instruction from the controller 10.

The reagent supplying means 6 has a first reagent supplying section 6a and a second reagent supplying section 6b. The first reagent supplying section 6a is used for supplying an acidic solution containing the molybdate ion such as an aqueous sulfuric acid acidic ammonium molybdate solution to the reaction container 1. The second reagent supplying section 6b is used for supplying a solution containing the fluorescent counter cationic pigment such as an aqueous Rhodamine B solution to the reaction container 1. Each of the first reagent supplying section 6a and the second reagent supplying section 6b has a reagent storing section (not shown) and reagent quantifying/adding means (not shown). The first reagent supplying section 6a and the second reagent supplying section 6b add respective reagents quantified in a prescribed amount at a prescribed timing to the reaction container 1 in accordance with the instruction from the controller 10.

As the above-mentioned sample or reagent quantifying/adding means, a syringe pump or the like is suitably applicable.

The operation of the measuring apparatus 100 will now be described. Upon receipt of an instruction from the input section 30 to start the measuring operation, the controller 10 causes the sample supplying section 5 to supply the sample solution quantified in a prescribed amount to the reaction container 1 in accordance with the measuring procedure and measuring conditions stored in the storage section 15. Then, the first reagent supplying section 6a of the reagent supplying means 6 is caused to quantify the sulfuric acid acidic ammonium molybdate solution in a prescribed amount and to add the quantified solution to the sample solution in the reaction container 1. Then, the second reagent supplying section 6b of the reagent supplying means 6 is caused to quantify the Rhodamine B solution in a prescribed amount and to add the quantified solution to the reagent solution (reaction solution) in the reaction container 1.

In the controller 10, the time measuring section 12 starts the time measurement simultaneously with the addition of the Rhodamine B solution to the reaction solution in the reaction container 1 by the second reagent supplying section 6b. The comparing section 13 compares the output signal from the fluorescence detector 3 and a reference signal corresponding to a set value of fluorescence intensity (target intensity to be attained). The time measuring section 12 discontinues the time measurement at the time when attainment of the output signal from the fluorescence detector 7 to the set value is detected by the comparing section 13.

As an alternative, in the controller 10, after the second reagent supplying section 6b adds the Rhodamine B solution to the reaction solution in the reaction container 1, the comparing section 13 compares the output signal from the fluorescence detector 3 and a first reference signal corresponding to a first set value of the fluorescence intensity (target intensity for starting measurement). Subsequently, at the time when attainment of the output signal from the fluorescence detector 3 to the first set value is detected by the comparing section 13, the time measuring section 12 starts the time measurement. The comparing section 13 then compares the output signal from the fluorescence detector 3 and a second reference signal corresponding to a second set value of fluorescence intensity (target intensity to be attained). The time measuring section 12 discontinues the time measurement at the time when attainment of the output signal from the fluorescence detector 3 to the second set value is detected by the comparing section 13.

The arithmetic operating section 14 calculates the concentration of silica, phosphorus or arsenic in the sample solution from the result of the time measurement obtained by the time measuring section 12, on the basis of the data (calibration curve) showing the relationship between the concentration of the ingredient to be measured (silica, phosphorus or arsenic) and the time stored in the storage section 15 in advance.

The data representing the relationship between the concentration of the ingredients to be measured and the time stored in advance in the storage section 15 of the controller 10 may have an arbitrary form of storage such as a calculation formula or table data. The data should preferably cover the conceivable range of concentrations of the ingredients to be measured in the sample solution. It should be readily understood by those skilled in the art that this data stored in the storage section 15 has only to be stored in the storage section 15 at least prior to actual measurement, not limited to storage in advance at the time of shipping from the factory of the measuring apparatus 100. The data may be stored by use of a prescribed reference solution through a so-called site calibration.

The method for calibration for determining the relationship between the concentration of silica, phosphorus or arsenic and the time may be one well known and used commonly by those skilled in the art. A general technique will be described. The relationship between the time (t) and the concentration (c) may be expressed by a function f:

$$c = f(t).$$

A number n of necessary reference solutions is determined from the number of coefficients of the function f depending upon the form of the function f. In general, the number of necessary reference solutions should include a zero adjustment solution and a span adjustment solution. The time (t) obtained from n-runs of the measurement and the known concentration (c) are incorporated into the function f respectively, and n-coefficients can be determined from nth simultaneous equations. Function f resulting from application of the individual coefficients is used as a calibration curve.

Figure 5:
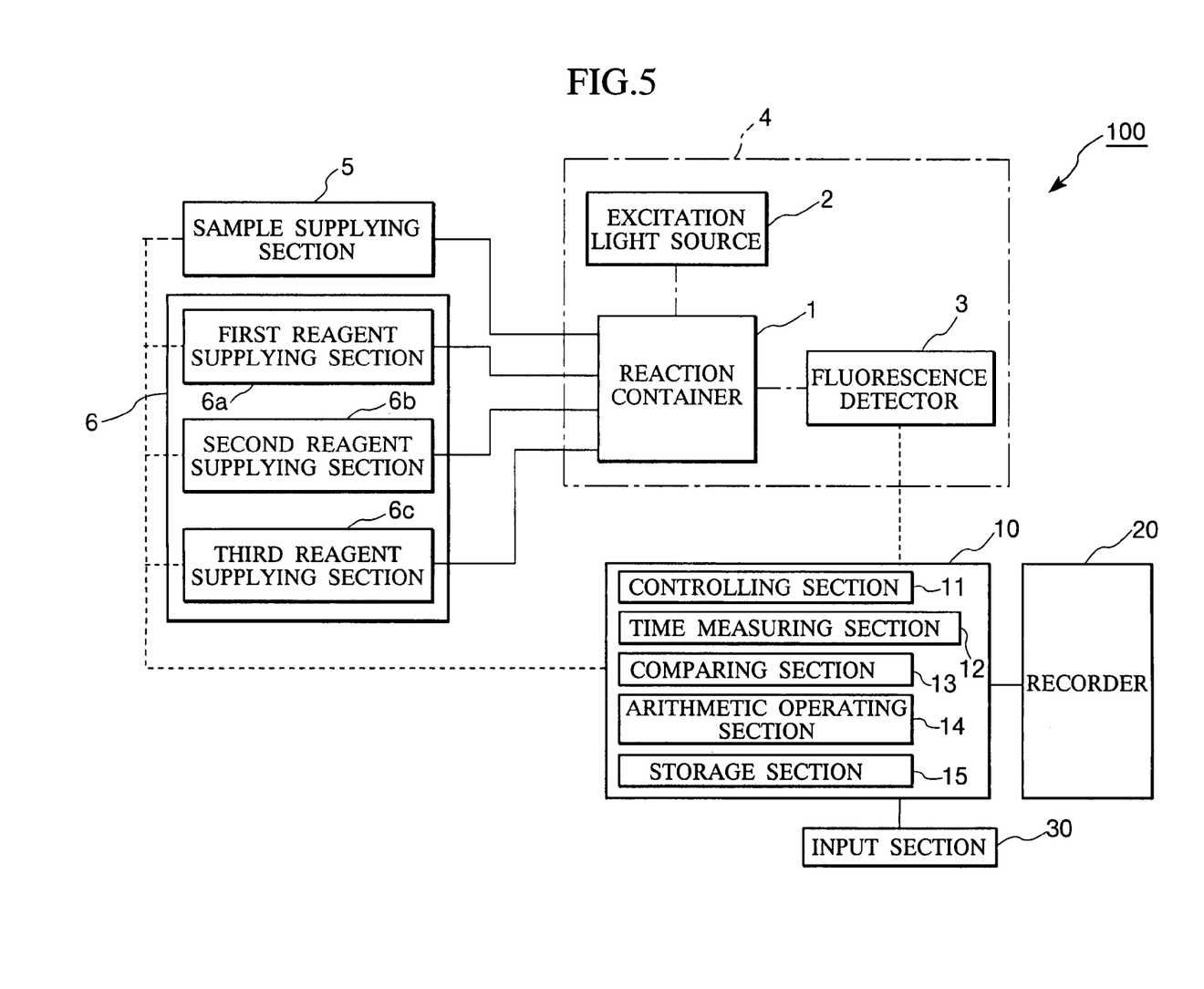
FIG. 5 is a schematic configuration diagram of another embodiment of the apparatus of the present invention for measuring trace ingredients in water.

In another embodiment of the measuring apparatus of trace ingredients in water, as shown in FIG. 5, the reagent supplying means 6 further comprises a third reagent supplying section 6c. The third reagent supplying section 6c has the same configuration as the first reagent supplying section 6a and the second reagent supplying section 6b described above, and has a reagent storing section and reagent quantifying/adding means.

The third reagent supplying section 6c can be used for adding an oxidizer, as desired upon measuring the concentration of arsenic, to the reaction solution in the reaction container 1. More specifically, in the operation of the measuring apparatus 100, after introducing the sample from the sample supplying section 5 into the reaction container 1, the oxidizer such as an aqueous potassium iodate solution is quantified and added to the sample solution in the reaction container 1 in a prescribed amount from the third reagent supply section 6c. Subsequently, the aqueous sulfuric acid acidic ammonium molybdate solution and the aqueous Rhodamine B solution are added from the first reagent supplying section 6a and the second reagent supplying section 6b, in the same manner as above, to the reaction solution in the reaction container 1, and the time is measured.

The third reagent supplying section 6c can be used for adding a decomposition agent of molybdophosphoric acid as desired to the reaction solution in the reaction container 1. When phosphorus is considered to coexist in the sample solution upon measuring the concentration of silica, after adding the aqueous sulfuric acid acidic ammonium molybdate solution from the first reagent supplying section 6a to the reaction solution in the reaction container 1, an aqueous solution of oxalic acid or tartaric acid serving as the decomposition agent of molybdic acid quantified in a prescribed amount is added from the third reagent supplying section 6c to the reaction solution in the reaction container 1. Subsequently, the aqueous Rhodamine B solution is added from the second reagent supplying section 6b to the reaction solution in the reaction container 1, and the time is measured.

In place of (or in addition to) the addition of the acidic ammonium molybdate solution by the first reagent supplying section 6a to the reaction solution, a strong acid supplying section having the same configuration as the first, the second and the third reagent supplying sections 6a, 6b and 6c may be provided separately, and prior to adding the ammonium molybdate solution to the sample solution, a strong acid in a prescribed amount may be added to the sample solution.

The controller 10 is not limited to being integrally disposed in the measuring apparatus 100 itself. The controller 10 may be a control device such as a personal computer which is communicably connected to the measuring apparatus 100, and operates in accordance with a program controlling the measuring apparatus 100. The recorder 20 described as being connected to the controller 10 may be a personal computer communicably connected to the measuring apparatus 100.

According to the measuring apparatus 100 shown in FIGS. 4 and 5, it is possible to carry out automatic measurement of ingredients to be measured in the sample solution, and to start or discontinue time measurement automatically in conjunction with the adding operation of the fluorescent counter cationic pigment to the reaction system, thus making it possible to conduct a very high-accuracy measurement simply, rapidly, and at a high sensitivity. However, the measuring method of the present invention is not limited to the use in the measuring apparatus 100 in the above-mentioned embodiment. The sample solution and some of the reagents may be introduced into the fluorescence detecting cell 1 after mixing them outside the cell 1, or the cell 1 may be arranged in the measuring apparatus 100 after supplying the sample solution and some of the reagents to the cell 1 and mixing them.

The present invention will now be described further in detail by means of some examples. The detailed description of measuring conditions and operations is not intended to limit the present invention to these embodiments, but is to present examples provided for better understanding of the present invention.

EXAMPLE 1

Aqueous solution samples in an amount of 5 ml containing silica (sodium hexafluorosilicate: extra-high grade; Wako Pure Chemical Industries, Ltd.) at the concentrations shown in Table 1 were each put in a fluorescence detecting cell; 5.0 M sulfuric acid (for precision analysis; Kanto Kagaku Co.) in an amount of 70 μl (0.07 M) was added thereto and the resultant mixture was shaken; and then, $3.0 \times 10^{-2}$ mol dm$^{-3}$ ammonium molybdate (for precision analysis; Wako Pure Chemical Industries, Ltd.) in an amount of 300 μl ($1.8 \times 10^{-3}$ mol dm$^{-3}$) was added thereto and the resultant mixture was shaken. Finally, $8.0 \times 10^{-5}$ mol dm$^{-3}$ Rhodamine B (Guaranteed Reagent Rhodamine B; Kanto Kagaku Co.) in an amount of 250 μl ($4.0 \times 10^{-6}$ mol dm$^{-3}$) was added. The time was measured from the addition of Rhodamine B until a prescribed fluorescence intensity (450 in this example) was reached.

In all the examples including this one, ultrapure water was used for diluting the reagents. Measurement of fluorescence was performed by the use of an RF-1500 type spectro-fluorophotometer made by Shimazu Corp., under conditions including an excitation wavelength (Ex.) of 556 nm, and a measuring wavelength (Em.) of 570 nm. The results are shown in Table 1 and FIG. 1.

TABLE 1

| Si (ppb) | TIME (min) |
|---|---|
| 0 | 8.33 |
| 0.5 | 7.12 |
| 1 | 2.62 |
| 1.5 | 2.55 |
| 2 | 1.95 |
| 3 | 0.75 |
| 4 | 0.72 |
| 5 | 0.68 |

The results shown in Table 1 and FIG. 1 indicate that the time required for attenuation of the fluorescence of Rhodamine B to a prescribed intensity along with ion association with molybdosilicate ion depends upon the silica concentration relative to trace silica concentration equal to or lower than 5 ppb. This correlation between silica concentration and time is applicable as a calibration curve for measuring the silica concentration in a water sample for which the concentration is unknown.

EXAMPLE 2

Measurements were carried out under quite the same conditions as Example 1, except that aqueous solution samples containing phosphorus (sodium dihydrogen phosphate: extra-high grade; Wako Pure Chemical Industries, Ltd.) at concentrations shown in Table 2 were used in place of the aqueous solution samples containing silica. The results are shown in Table 2 and FIG. 2.

TABLE 2

| P (ppb) | TIME (min) |
|---|---|
| 0 | 6.32 |
| 1 | 1.78 |
| 2 | 0.95 |

The results shown in Table 2 and FIG. 2 indicate that the time required for the fluorescence of Rhodamine B to be attenuated to a prescribed intensity along with ion association with molybdophosphate ion depends upon the phosphorus concentration relative to trace phosphorus concentration equal to or lower than 2 ppb. This correlation between phosphorus concentration and time is applicable as a calibration curve for measuring the phosphorus concentration in a water sample for which the concentration is unknown.

EXAMPLE 3

Aqueous solution samples in an amount of 5 ml containing arsenic (disodium hydrogen arsenate: extra-high grade; Kanto Kagaku Co.) at the concentrations shown in Table 3 were each put in a fluorescence detecting cell; $4.0 \times 10^{-2}$ mol $dm^{-3}$ potassium iodate (extra-high grade; Wako Pure Chemical Industries, Ltd.) in an amount of 250 µl ($2.0 \times 10^{-3}$ M) was added thereto and the resultant mixture was shaken; then, 5M sulfuric acid (for precision analysis; Kanto Kagaku Co.) in an amount of 140 µl (0.14 M) was added thereto and the resultant mixture was shaken; and then, $2.5 \times 10^{-2}$ mol $dm^{-3}$ ammonium molybdate (for precision analysis; Wako Pure Chemical Industries, Ltd.) in an amount of 1,000 µl ($5.0 \times 10^{-3}$ M) was added thereto and the mixture was shaken. Finally, $2.0 \times 10^{-4}$ mol $dm^{-3}$ Rhodamine B (Guaranteed Reagent Rhodamine B; Kanto Kagaku Co.) in an amount of 100 µl ($4.0 \times 10^{-6}$ M) was added. The time required was measured from the addition of Rhodamine B until a prescribed fluorescence intensity (450 in this example) was reached. The results are shown in Table 3 and FIG. 3.

TABLE 3

| As (ppm) | TIME (min) |
|---|---|
| 0.01 | 12.17 |
| 0.04 | 7.50 |
| 0.1 | 6.33 |
| 1 | 0.70 |

The results shown in Table 3 and FIG. 3 indicate that the time required for the fluorescence of Rhodamine B to be attenuated to a prescribed intensity along with ion association with molybdoarsenate ion depends upon the arsenic concentration relative to trace arsenic concentration equal to or lower than 1 ppm. This correlation between arsenic concentration and time is applicable as a calibration curve for measuring the arsenic concentration in a water sample for which the concentration is unknown.

INDUSTRIAL APPLICABILITY

According to the present invention, as described above, the method for measuring trace ingredients in water comprises the steps of adding a molybdate ion to a sample solution under an acidic condition, then adding a fluorescent counter cationic pigment thereto, and measuring the time required for the fluorescence emitted by the resultant solution to be attenuated to a prescribed intensity, thereby measuring the concentration of silica, phosphorus or arsenic. The apparatus for realizing the method of the present invention comprises an excitation light source which irradiates excitation light to the solution obtained by adding a molybdate ion to a sample solution under an acidic condition and then adding a fluorescent counter cationic pigment thereto; a fluorescence detector which detects the fluorescence emitted by the solution; time measuring means for measuring the time required for the fluorescence detected by the fluorescence detector to be attenuated to a prescribed intensity; and control means for determining the concentration of silica, phosphorus or arsenic in the sample solution from the result of time measurement by the time measuring means. As a result, it is possible to detect and quantitatively determine silica, phosphorus or arsenic in the sample solution simply, rapidly, at a high sensitivity and at a high accuracy (high resolution), and to cope with the automatic measurement of trace silica, phosphorus or arsenic in water.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for measuring trace ingredients in water comprising the steps of adding a molybdate ion to a sample solution under an acidic condition, then adding a fluorescent counter cationic pigment thereto, and measuring a time required for fluorescence emitted by a resultant solution to be attenuated to a prescribed intensity, thereby measuring a concentration of silica, phosphorus or arsenic contained in the sample solution.

2. The method according to claim 1, wherein the time measurement is started simultaneously with the addition of said fluorescent counter cationic pigment, and the time required for the fluorescence to be attenuated to a prescribed intensity is measured.

3. The method according to claim 1, wherein the time required for the fluorescence to be attenuated from a first intensity to a second intensity, after adding said fluorescent counter cationic pigment, is measured.

4. The method according to claim 1, wherein, upon measuring the concentration of arsenic in the sample solution, an oxidizer is added to the sample solution prior to adding said molybdate ion.

5. The method according to claim 4, wherein said oxidizer comprises an iodate.

6. The method according to claim 1, wherein, upon measuring the concentration of silica in the sample solution, a decomposition agent of molybdophosphoric acid is added after adding said molybdate ion, and thereafter said fluorescent counter cationic pigment is added.

7. The method according to claim 6, wherein said decomposition agent of molybdophosphoric acid comprises oxalic acid or tartaric acid.

8. The method according to claim 1, wherein said acidic condition is achieved by mixing the sample solution with a strong acid.

9. The method according to claim 1, wherein said fluorescent counter cationic pigment is Rhodamine B.

* * * * *